(12) United States Patent
McAdams

(10) Patent No.: US 7,718,823 B2
(45) Date of Patent: May 18, 2010

(54) TOLUATE ESTER FOR USE AS REACTIVE AND NON-REACTIVE DILUENT IN POLYMER APPLICATIONS

(75) Inventor: Carina Araullo McAdams, Wilmington, NC (US)

(73) Assignee: Invista North America S.A R. L., Wilmington, DE (US)

( * ) Notice: Subject to any disclaimer, the term of this patent is extended or adjusted under 35 U.S.C. 154(b) by 762 days.

(21) Appl. No.: 10/557,103

(22) PCT Filed: May 13, 2004

(86) PCT No.: PCT/US2004/015082

§ 371 (c)(1),
(2), (4) Date: Nov. 15, 2005

(87) PCT Pub. No.: WO2004/104079

PCT Pub. Date: Dec. 2, 2004

(65) Prior Publication Data

US 2006/0223925 A1 Oct. 5, 2006

Related U.S. Application Data

(60) Provisional application No. 60/470,911, filed on May 15, 2003.

(51) Int. Cl.
*C07C 67/02* (2006.01)
(52) U.S. Cl. ........................................ 560/92
(58) Field of Classification Search ........................ None
See application file for complete search history.

(56) References Cited

U.S. PATENT DOCUMENTS

| 2,585,448 | A | * | 2/1952 | Emerson et al. | 106/316 |
| 4,112,240 | A | * | 9/1978 | Hulsmann et al. | 560/112 |
| 4,293,480 | A | | 10/1981 | Martin et al. | |
| 4,615,372 | A | | 10/1986 | Kopac et al. | |
| 4,656,214 | A | | 4/1987 | Wickson | |
| 5,990,214 | A | * | 11/1999 | Arendt et al. | 524/296 |
| 6,184,278 | B1 | * | 2/2001 | Arendt et al. | 524/284 |
| 6,291,550 | B1 | | 9/2001 | Chen et al. | |

FOREIGN PATENT DOCUMENTS

| GB | 947764 | * | 1/1964 |
| WO | WO02/083621 | | 10/2002 |

* cited by examiner

*Primary Examiner*—Karl J Puttlitz

(57) ABSTRACT

This invention relates to toluate ester compositions and their use as solvent, plasticizers, extender and/or diluents in binder formulations, a method of producing such ester compositions, as well as polymer compositions containing such liquid ester compositions. The method of making toluate based esters by reacting methyl-p-toluate with ethylene glycol, diethylene or triethylene glycol, butanediol, etc. More particularly, this invention relates to the mono- or di-ester of methyl toluic acid with a diol containing 2 to 6 carbon atoms that are low viscosity liquids at 25° C. The most common polymer that employs plasticizer is polyvinyl chloride (PVC). Typical amounts of plasticizer in PVC are from about 3 wt. % to about 50 wt. %. Phenolic resins generally require solvents, diluents and/or extenders that reduce the volatility and viscosity of the resin, especially when it is used in building and automotive products. Typical amounts of solvent are from about 5 wt. % to about 65 wt. %.

9 Claims, No Drawings

TOLUATE ESTER FOR USE AS REACTIVE AND NON-REACTIVE DILUENT IN POLYMER APPLICATIONS

CROSS REFERENCE

This invention claims the priority of U.S. Provisional Application 60/470,911 filed May 15, 2003.

BACKGROUND OF THE INVENTION

1) Field of the Invention

This invention relates to liquid toluate-based ester compositions and their use as plasticizers, extenders or diluents in polymer formulations, a method of producing such ester compositions, as well as polymer compositions containing such liquid ester compositions. More particularly, this invention relates to the mono- or di-ester of methyl toluic acid with a diol containing 2 to 6 carbon atoms that are low viscosity liquids at 25° C. This invention also relates to the aforementioned esters modified with long chain hydrocarbon based extenders such as tall oil fatty acids or natural oils. The most common polymer that employs plasticizer is polyvinyl chloride (PVC). Typical amounts of plasticizer in PVC are from about 3 wt. % to about 50 wt. %. Phenolic resins generally require a hydrocarbon solvent/diluent/extenders that reduces the volatility and viscosity of the resin, especially when it is used in building or automotive products. Typical amounts of the aforementioned esters used as solvent/diluent/extender are from about 5 wt. % to about 65 wt. %.

2) Description of Prior Art

Esters derived from benzoic, substituted benzoic and toluic acid with aliphatic alcohols, and the methods for preparation, have been described in the prior art. These esters are primarily used as plasticizers for polymers to facilitate processing and increase flexibility and toughness. Homo- and co-polymers of polyvinyl chloride (PVC) account for the majority of the plasticizer usage. The most common plasticizer, dioctyl phthalate (DOP), has been the subject of negative environmental and toxicological studies and is a high cost additive. Benzoate plasticizers (dipropylene glycol dibenzoate, diethylene glycol dibenzoate) have been introduced as plasticizers but only have moderate compatibility with PVC.

U.S. Pat. No. 2,585,448 to Emerson et al. discloses mixtures of esters prepared by esterifying diols such as diethylene glycol, triethylene glycol with aromatic monocarboxylic acids such as benzoic acid and alkyl substituted benzoic acid. These esters are used as plasticizers.

U.S. Pat. No. 4,656,214 to Wickson discloses diesters having: 1) linear glycols containing from 2 to 8 carbon atoms, 2) a first carboxylic acid of the formula $R^1R^2R^3C(O)OH$, and 3) a second carboxylic acid of the formula $R^5C(O)OH$, wherein $R^1$ and $R^2$ are individually selected from alkyl containing from 1 to 4 carbon atoms, $R^3$ is hydrogen or alkyl from 1 to 6 carbon atoms, $R^5$ is selected from the group consisting of phenyl, mono- di- and trialkyl-substituted phenyl containing from 9 to 12 carbon atoms and $-(CH_2)_n Ph$ where Ph is phenyl and the value of n is from 1 to 6, inclusive. The esters contain from 16 to 19 carbon atoms and are useful as stain-resistant plasticizers for polyvinyl chloride.

U.S. Pat. No. 5,990,214 to Arendt et al. discloses liquid compositions of mixtures of esters derived from diethylene and triethylene glycol and benzoic or toluic acid. These esters are useful as plasticizers for PVC.

WO 02/083621 to Lang et al. discloses mixed esters prepared in a single step reaction from diols such as diethylene glycol, benzoic acid and an aliphatic acid such as lauric acid. These are liquid at room temperatures and are useful as plasticizers for PVC.

These ester compositions are still slightly volatile, and there is a need for ester compositions with lower volatility than commonly used materials such as dibutyl ester. Also these ester compositions are comparatively expensive and are still somewhat environmental sensitive and toxicological adverse. Thus there is a need for lower cost materials which are less environmentally sensitive and are not toxic.

Phenolic resins, including furan resins and phenolic urethanes, are used as binders for building products, wood products, insulation, foundry materials, abrasives and friction materials. In these formulations hydrocarbon solvents are used as diluents to reduce the viscosity of the phenolic resins. There is a need for diluents that have low volatility, or that can be incorporated into the resin, in order to reduce the Volatile Organic Compound (VOC) level. There is a need for diluents which produce low smoke in foundry applications.

U.S. Pat. No. 4,615,372 to Kopac et al describes a typical phenolic resin binder that contains 45-50 wt. % solvents, usually a mixture of aromatic hydrocarbons and moderately polar solvents.

U.S. Pat. No. 4,293,480 to Martin et al discloses a foundry binder based on a polyol, an isocyanate urethane polymer and a urethane catalyst. Again a polar solvent is used in this composition.

U.S. Pat. No. 6,291,550 to Chen et al discloses a solventless polyurethane no bake foundry binder, using polyether polyol, isocyanate and a urethane catalyst. In this invention, glycol such as triethylene glycol is used as a reactive diluent in the binder.

There is also a need for diluents and solvents that reduce the VOC level in other formulations such as paints, inks, elastomers, adhesives, foundry molding compositions, etc.

There is also a need for low viscosity dye carriers for textiles, polyurethanes, and paper applications which are more economical than existing carriers.

SUMMARY OF THE INVENTION

The present invention is based on the discovery that diethylene glycol esters or triethylene glycol esters of toluic acid, prepared from the methyl-p-toluate have low volatility and low melting points. In addition to being used as plasticizers, they also can act as diluents or reactants to reduce viscosity in foundry binders, casting resins and polyurethane applications. The methyl-p-toluate can conveniently be obtained from a Witten dimethyl terephthalate process.

This invention relates to the mono- or di-ester of methyl toluic acid with a diol containing 2 to 6 carbon atoms that are low viscosity liquids at 25° C.

This invention also relates to compositions of polymer and the esters of toluic acid.

In the broadest sense, the present invention relates to mono- or diester prepared from the reaction of toluic acid or its ester, with ethylene, diethylene, or triethylene glycol, butanediol, and other aliphatic diols, with or without long chain hydrocarbon based extenders such as tall oil fatty acids (including modified tall oil like methyl ester tall oil) and/or natural oils. Natural oils used can be in the form of canola oil, castor oil, clove oil, coconut oil, corn oil, cottonseed oil, jojoba oil, linseed oil, olive oil, palm oil, peanut oil, safflower oil, sesame oil, soybean oil, and sunflower oil.

In the broadest sense, the invention relates to a method of producing a low viscosity, low volatility, and low melting point ester by reacting methyl-p-toluate with diethylene or triethylene glycol or by reacting methyl-p-toluate with diethylene or triethylene glycol and an aliphatic-based extender such as tall oil fatty acids (including modified tall oil like methyl ester tall oil) and/or natural oils such as canola oil, castor oil, clove oil, coconut oil, corn oil, cottonseed oil, jojoba oil, linseed oil, olive oil, palm oil, peanut oil, safflower oil, sesame oil, soybean oil, and sunflower oil.

In the broadest sense, the present invention also relates to a composition of polymer and mono- or di-ester of methyl-p-toluate with a diol containing 2 to 6 carbon atoms that are low viscosity liquids at 25° C.

In the broadest sense, the invention also relates to foundry molding composition comprising: sand; either phenol-formaldehyde resin or polyether polyol, either of which contains toluate based reactive or nonreactive diluent; polyisocyanate; and catalyst.

DETAILED DESCRIPTION OF THE INVENTION

Methyl-p-Toluate (MpT) can be transesterified, using conventional catalysts (such as manganese, magnesium, and/or cobalt), with diols to form the mono- or di-ester. A common diol is diethylene glycol or triethylene glycol, but the pure toluate esters have high melting points and thus the selection of the diol depends on its ability to withstand these high processing temperatures.

In the Witten process for producing dimethyl terephthalate (DMT), p-xylene is converted through oxidation and esterification with methanol to DMT. After the first oxidation process a stream that is rich in MpT is produced that is normally recycled for further oxidation. It is found that this stream can be esterified with diols to produce toluic esters that are liquid at room temperature and have low volatility. It is also found that these esters can be used as extenders or components in numerous applications such as binders, foamed applications, etc.

The preferred ester is either the glycol mono- or di-toluate. The di-ester can be used as a non-reactive plasticizer or diluent, and the reactive monoester can be reacted into the phenolic resin or urethane. When used as a diluent it is necessary for the viscosity of the ester to be below about 0.35 pascal second (Pa·s) (so that the total system viscosity is in a useful range), and preferably <0.25 Pa·s, and more preferably <0.20 Pa·s. In polyurethane formulations it is preferred that the acid number is less than 4 in order to minimize the quantity of catalyst required.

These toluates are also useful as diluents in binder applications which use hydrocarbon based solvents as extenders. In order to improve the compatibility of these esters with systems that contain hydrocarbon solvents, natural oils, or tall oil fatty acids (including modified tall oil like methyl ester tall oil) may be reacted into the esters. Suitable natural oils are canola oil, castor oil, clove oil, coconut oil, corn oil, cottonseed oil, jojoba oil, linseed oil, olive oil, palm oil, peanut oil, safflower oil, sesame oil, soybean oil, and sunflower oil. Preferred is soybean oil. The amount of natural oil or tall oil fatty acid that may be added to the toluate ester is from about 1 to about 25 wt. % of the total of toluate ester and natural oil and/or tall oil fatty acid.

The most common polymer that employs plasticizer is polyvinyl chloride (PVC). Typical amounts of plasticizer in PVC are from about 3 wt. % to about 50 wt. % of the total weight of the composition of PVC. The toluate ester can be added as the primary plasticizer or as a cosolvent in the PVC application.

Phenolic resins generally require diluents or extenders that reduce the volatility and viscosity of the resin, especially when they are used in building or automotive products. Typical amounts of toluate ester solvent are from about 10 wt. % to about 65 wt. % of the composition of phenolic resin and toluate ester.

EXAMPLES

The process stream, from a Witten DMT process, used as the source of MpT had the composition (weight %) set forth in Table I. This data represents the range of average monthly composition of the components over a 5-year period.

TABLE I

| Compound | Low value | High Value |
| --- | --- | --- |
| Methyl-p-toluate | 68 | 84 |
| Dimethyl terephthalate | 6 | 20 |
| Methyl-p-formyl benzoate | 2 | 6 |
| p-toluic acid | 1 | 5 |
| Methyl benzoate | 1 | 3 |

The aforementioned toluate esters can also be prepared from high purity methyl-p-toluate. For example, a product stream containing 98% methyl-p-toluate can be obtained by distillation of the process stream described in Table I.

The acid number (mg KOH/g) was determined by ASTM 4662-98.

The viscosity was measured by ASTM 4878-98 at 25° C.

The total VOC per ton of sand for each foundry aggregate was measured by preparing a mold with 6 inch×6 inch×0.75 inch dimension. The mold was stored at 40° C. in an oven for 24 to, 72 hours, or after a constant weight is obtained. The weight loss after incubation was measured to report the pounds VOC per ton sand. A low number means that the product has a low volatility.

The tensile strengths of the dog bone shapes were measured on a Universal Sand Tester according to standard procedures. Measurements were carried out after storage in a constant room temperature at 0.5 hr, 1.5 hrs, 3 hrs, 6 hrs, and 24 hrs, and also after 24 hours storage at a relative humidity (RH) of 98%. The tensile strength of the dog bones is a measure of the binding strength of the mixture of sand and binder containing the toluate esters.

Example 1

An ester produced from 500 g of the process stream set forth in Table I, and 150 g of diethylene glycol (DEG) were heated with 0.04 wt. % Tyzor catalyst in a reactor. The reactor contents were stirred and equipped with a water-cooled reflux condenser. The contents of the reactor were rapidly heated to 180° C., and then gradually heated to 220° C. over a 3 hour period. After cooling to ambient temperature, the product had an acid number of 0.35 and a viscosity of 0.25 Pa·s.

Example 2

The process of Example 1 was repeated with a reactor charge of 400 g of the process stream, and 180 g of diethylene glycol (DEG), 100 g of tall oil fatty acid, and 0.27 g of Tyzor catalyst. The temperature was raised up to 240° C. and the contents were discharged into a holding tank and the acid number and viscosity were measured when the contents returned to ambient temperature. The product had an acid number of 3.91 and a viscosity of 0.30 Pa·s. The acid number of the material can be reduced by reacting propylene carbonate and a tertiary amine with the toluate ester at 235° C. for 30 minutes.

Example 3

The process of Example 1 was repeated with a reactor charge of 300 g of the process stream, and 150 g of DEG, and 0.18 g of Tyzor catalyst. When the temperature reached 220° C. after about 1 hour, 100 g soybean oil was added and the reaction mixture held at 220° C. for 2 additional hours. The contents of the reactor were discharged into a holding tank and the acid number and viscosity were measured when the contents returned to ambient temperature. The product had an acid number of 1.1 and a viscosity of 0.07 Pa·s.

Example 4

Example 3 was repeated with the replacement of the DEG with 100 g triethylene glycol. The product had a viscosity of 0.04 Pa·s.

Example 5

Example 3 was repeated with the replacement of the DEG with ethylene glycol. The product had a viscosity of 0.10 Pa·s.

Any of these toluate esters (or a mixture of them) can be used to replace the typical solvents used in polymer compositions such as binders in foundry applications.

Experimental Procedure for Examples 6-14

Foundry sand mixes were prepared by first mixing 2000 parts sand with the phenol-formaldehyde resin or polyether polyols with solvent and/or reactive diluents (hereafter Part I) and catalyst for 2 minutes. The sand was a round grain silica supplied by US Silica, ~55 AFS fineness, except where the sand is specified as being from another source. Then an organic polyisocyanate having a functionality of 2.5 to 2.7 and optionally diluents (hereafter Part II) was added and mixed with the sand aggregate for 60 seconds. The resulting foundry mixes were used to fill core boxes to make dog bone testing samples for tensile strength measurements and mold samples for volatile organic compounds (VOC) measurements.

Both the work time and strip time (in minutes) were measured for each foundry mix using a Green Hardness "B" Scale Tester. The work time and strip time are the time intervals after mixing PART II and the time when the foundry shape reaches 35 psi and 75 psi, respectively. In the runs included in this patent, the catalyst levels were adjusted to obtain a work time and strip time of about 4 to 10 minutes, and 5 to 12 minutes, respectively.

Examples 6-9

The following examples illustrate the use of toluate esters as reactive solvents in binder no-bake foundry systems to reduce total volatile organic emissions in a foundry process. The liquid phenolic resin (LPR) control contained about 10 to 30% aromatic hydrocarbons ($C_9$ to $C_{11}$) and 10 to 30% mixture of dimethyl succinate, glutarate and adipates. Mixture A is a phenolic resin base (PRB) containing 50 wt. % of a toluate ester with OH number of <100 (commercially available from KoSa under the trade name Teraflex® 424S). The viscosity of the PRB used in this study was >100 Pa·s. Blend solutions of the LPR and Mixture A were prepared at 75/25, 50/50, 25/75 ratio to obtain 25%, 50% and 75% solvent replacement of a commercial product with Teraflex 424S, respectively. The LPR was used as a control. The polymeric isocyanate used in Part II, has a functionality of 2.7, and contained diphenylmethane 4,4'-diisocyanate and polymeric diphenylmethane 4,4'-diisocyanate. The catalyst used in this study was 4-phenylpropylpyridine in aromatic hydrocarbon carrier ($C_9$ to $C_{11}$). The test conditions for these Examples are below. The results are shown in Table II.

Binder level: 1.75% BOS (based on sand)
MixRatio: 1:1 (Part I: Part II)
Catalyst: 2.3% to 3% BOB (based on binder)

TABLE II

| Description | Example 6 PR Control | Example 7 75% PR Control and 25% Mixture A | Example 8 50% PR Control and 50% Mixture A | Example 9 25% PR Control and 75% Mixture A |
|---|---|---|---|---|
| Solvent Replacement with Teraflex 424S | 0% | 25% | 50% | 75% |
| Part I Viscosity, Pa·s | 0.14 | 0.22 | 0.30 | 0.41 |
| Catalyst, BOB Reactivity | 2.3% | 3.2% | 3.2% | 3.2% |
| Work Time, minutes | 7.63 | 6.67 | 6.67 | 7.08 |
| Strip Time, minutes | 9.58 | 8.22 | 8.83 | 10.10 |
| Tensile Strength, psi | | | | |
| 0.5 hr | 128 | 149 | 111 | 91 |
| 1.5 hr | 221 | 220 | 209 | 198 |
| 3.0 hr | 249 | 246 | 236 | 229 |
| 6 hr | 268 | 286 | 281 | 269 |
| overnight | 320 | 306 | 326 | 325 |
| overnight, 98% RH | 96 | 91 | 79 | 87 |
| VOC, pounds/ton sand | 3.46 | 2.87 | 2.30 | 1.13 |

The results above indicate that Teraflex 424S can be added to phenolic urethane binders to reduce the VOC emissions of the foundry aggregate. There is an optimum Teraflex 424S loading (10 to 25%) usable for no-bake foundry binder system without compromising tensiles of the test cores and viscosity of Part I. Toluate esters are highly aromatic and can be prepared as reactive diluent (Teraflex 424S) and/or nonreactive plasticizer. Teraflex 424S is a reactive diluent that is compatible with current phenolic urethane binder system and will not plasticize the sand aggregate in a manner other than commonly used reactive and nonreactive plasticizers such as dibasic esters (DBE) and glycols would.

Toluate esters can be used to replace solvent package in foundry applications to provide a rigid foundry aggregate. The supporting data is shown in Table III.

Test Conditions:

Binder level: 1.75% BOS
Mix Ratio: 1:1
Catalyst: 2.3% BOB purposes. The test conditions and results are shown in Table IV.

Test Condition:
Binder level: 1.75% BOS
Mix Ratio: 42:58 to 53:47
Catalyst: 3.5 to 5%, BOB

TABLE IV

|  | Example 11, Control | Example 12 | Example 13 | Example 14 | Example 15 |
|---|---|---|---|---|---|
| Part I | 50/50 of PEP and TEG | 50/50 of PEP and TEG | 50/50 of PEP and Teraflex 424S | 50/50 of PEP and TEG | 50/50 of PEP and Teraflex 424S |
| Reactive Solvent | TEG | TEG | Teraflex 424S | TEG | Teraflex 424S |
| Part I Viscosity, Pa·s | 0.12 | 0.12 | 0.18 | 0.12 | 0.18 |
| Catalyst[1] | A | A | A | B | B |
| I:II Ratio Mix | 42:58 | 53:47 | 53:47 | 53:47 | 53:47 |
| Catalyst Level, BOB | 3.5% | 4.5% | 4.5% | 5.0% | 5.0% |
| Reactivity, minutes |  |  |  |  |  |
| Work Time | 4.04 | 4.00 | 5.08 | 4.30 | 4.45 |
| Strip Time | 7.23 | 8.00 | 9.55 | 9.15 | 9.47 |
| Tensile Strength, psi |  |  |  |  |  |
| 0.5 hr | 194 | 32 | 240 | 26 | 113 |
| 1.5 hr | 197 | 22 | 331 | 22 | 235 |
| 3.0 hr | 157 | 20 | 329 | 20 | 259 |
| 6 hr | 167 | 21 | 303 | 18 | 271 |
| overnight | 167 | 23 | 351 | 16 | 281 |
| overnight, 98% RH | 42 | 8 | 74 | 4 | 62 |

[1] A is Huntsman's Z80 catalyst dissolved in DPG. B is a mixture of trimerization catalyst and Z80 in DPG.

TABLE III

|  | Binder A | Binder B |
|---|---|---|
| Work Time (min.) | 11 | 7 |
| Strip Time (min.) | 22 | 12 |
| VOC (1 day), lb/ton | 2.7 | 0 |
| Tensiles, psi 2 hr | 24 | 76 |
| Over Night | 100 | 264 |
| Observation | flexible, pliable | rigid |

A = Part I composition: 50% PRB, 20% DBE, 30% Teraflex 422M
B = Part I composition: 50% PRB, 5% DBE, 45% Teraflex 422M Examples 10-14

The following examples illustrate the use of toluate esters as reactive diluent in solventless polyurethane no-bake foundry binders to improve binder strength. An all-polyether polyol (PEP) was used as the control for this study. The control is based on the binder patent example described in U.S. Pat. No. 6,291,550. Part I consists of polyether polyol—50% BASF's Pluracol TP440 in TEG, Part II is isocyanate—BASF-Lupranate M20S (2.7 functionality) and the catalyst package is a nobake catalyst known to contain tris(3-dimethylamino)propylamine in dipropylene glycol (DPG). Teraflex 424S (a toluate ester having OH number of about 250) was used as a direct replacement of TEG and the test conditions with respect to mix ratio Part I: Part II and catalysis were varied to obtain similar work time/strip time for comparative purposes.

Based on the data shown in Table IV, toluate esters such as Teraflex 424S can be used in solventless polyurethane systems as a replacement to commonly used diluents such as glycol to improve the tensile properties of the foundry system. At 50% loading, toluate esters cuts the viscosity of the PEP polyol to a level usable to the industry (<0.2 Pa·s), and to the same extent as the commonly used reactive solvents such as a TEG, DEG, etc. However, unlike TEG, toluate esters yield much higher tensile strengths in the test cores over TEG. Also, because toluate esters have lower hydroxyl value compared to TEG (<100 vs. 748 OH value for Teraflex 424S and TEG, respectively), a lower level of isocyanate (PART II) is required to react with the toluate based reactive diluent. This is evident in Table IV which shows less isocyanate required to obtain the optimum tensile strength in PEP systems containing Teraflex 424S. The PEP/TEG system requires 58 parts isocyanate per 100 parts binder system, whereas PEP/Teraflex 424S systems consistently show higher tensiles at 47 parts isocyanate loading per 100 parts binder system.

The effect of Teraflex 424S is similar to that of loading aromatic polyester polyol in PEP binders described in U.S. Pat. No. 6,291,550. The patent shows improved early tensile strengths on test cores from PEP based binders containing aromatic polyester polyols compared to the control (all PEP). The use of aromatic polyester polyols, however, poses a processing challenge due to their relatively high viscosity. Toluate esters such as Teraflex 424S combines the properties of highly aromatic polyester polyols (Terate®, Stepanpol®, Terol®) and that of common diluents used to lower viscosity such as glycol and DBE.

Thus it is apparent that there has been provided, in accordance with the invention, a low viscosity, low volatility, and low melting point ester useful as a plasticizers for PVC or as diluents/extenders in binder compositions, that fully satisfies the objects, aims and advantages set forth above. While the invention has been described in conjunction with specific embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the invention.

What is claimed is:

1. A toluate based ester composition useful as a plasticizer, extender, or diluent in polymer formulations, said composition comprising: a mixture of esters prepared from the reaction of a methyl-p-toluate enriched stream of a Witten dimethyl terephthalate process, said methyl-p-toluate enriched stream containing in addition to methyl-p-toluate, dimethyl terephthalate, methyl-p-formyl benzoate, toluic acid and no more than 3 wt % of methyl benzoate, with ethylene glycol, diethylene glycol, triethylene glycol, or butanediol, said composition having a viscosity of less than 0.35 pascal second at 25° C.

2. The toluate based ester composition of claim 1, wherein said ester composition has a viscosity of less than about 0.25 pascal second.

3. The toluate based ester composition of claim 1, wherein said methyl-p-toluate enriched stream of a Witten dimethyl terephthalate process comprises from about 6 to 20 wt % of dimethyl terephthalate, from about 2 to 6 wt % of methyl-p-formyl benzoate, from about 1 to 5 wt % of p-toluic acid and from about 1 to 3 wt % of methyl benzoate in addition to methyl-p-toluate.

4. The toluate based ester composition of claim 1, wherein said methyl-p-toluate enriched stream comprises from about 68 wt % to 84 wt % of methyl-p-toluate.

5. The toluate based ester composition of claim 1, further including tall oil fatty acids or modified tall oil fatty acids.

6. The toluate based ester composition of claim 1, further including canola oil, castor oil, clove oil, coconut oil, corn oil, cottonseed oil, jojoba oil, linseed oil, olive oil, palm oil, peanut oil, safflower oil, sesame oil, soybean oil, or sunflower oil.

7. A toluate based ester composition useful as a plasticizer, extender, or diluent in polymer formulations, said composition comprising: a mixture of esters prepared from the reaction of a methyl-p-toluate enriched stream comprising methyl-p-toluate, from about 6 to 20 wt % of dimethyl terephthalate, from about 2 to 6 wt % of methyl-p-formyl benzoate, from about 1 to 5 wt % of p-toluic acid and from about 1 to 3 wt % of methyl benzoate, with diethylene glycol or triethylene glycol, said composition having a viscosity of less than 0.35 pascal second at 25° C.

8. A toluate based ester composition according to claim 7 wherein said methyl-p-toluate enriched stream comprises from about 68 wt % to 84 wt % of methyl-p-toluate.

9. A toluate based ester composition according to claim 7 which further includes tall oil fatty acids, modified tall oil fatty acids, canola oil, castor oil, clove oil, coconut oil, corn oil, cottonseed oil, jojoba oil, linseed oil, olive oil, palm oil, peanut oil, safflower oil, sesame oil, soybean oil, or sunflower oil.

* * * * *